United States Patent [19]
McVicker

[11] 3,946,082
[45] Mar. 23, 1976

[54] PREPARATION OF ZEROVALENT PHOSPHINE SUBSTITUTED RHODIUM COMPOUNDS AND THEIR USE IN THE SELECTIVE CARBONYLATION OF OLEFINS

[75] Inventor: Gary B. McVicker, Westfield, N.J.

[73] Assignee: Exxon Research & Engineering Co., Linden, N.J.

[22] Filed: Feb. 6, 1974

[21] Appl. No.: 439,849

Related U.S. Application Data

[62] Division of Ser. No. 237,891, March 24, 1972, abandoned.

[52] U.S. Cl. ...... 260/604 HF; 260/598; 260/601 H; 260/602; 260/486 R; 260/526 R; 260/465.1; 260/449 R; 260/551 R; 260/615 R
[51] Int. Cl.² ......................................... C07C 45/08
[58] Field of Search ........................... 260/604 HF

[56] References Cited
FOREIGN PATENTS OR APPLICATIONS
1,207,561  10/1970  United Kingdom .......... 260/604 HF

OTHER PUBLICATIONS

Cotton et al., Advanced Inorganic Chem., 2nd Edit., p. 1010, 1966.

Chaston et al., Chemical Communications, p. 964, 1967.

Primary Examiner—James O. Thomas, Jr.
Assistant Examiner—R. H. Liles
Attorney, Agent, or Firm—John P. Corcoran

[57] ABSTRACT

A process for preparing oxygenated products comprising aldehydes, which have high normal to branched-chain isomer ratios. The process involves using particularly characterized rhodium-containing complex catalysts under a specific combination of carefully controlled reaction conditions. The product aldehydes as made above may be condensed and hydrogenated to form saturated aldehyde dimers thereof.

6 Claims, No Drawings

PREPARATION OF ZEROVALENT PHOSPHINE SUBSTITUTED RHODIUM COMPOUNDS AND THEIR USE IN THE SELECTIVE CARBONYLATION OF OLEFINS

CROSS REFERENCE TO RELATED APPLICATIONS

This application is a divisional of copending application Ser. No. 237,891 filed Mar. 24, 1972, now abandoned.

This invention relates to an improved process for the preparation of organic oxygenated compounds containing a high ratio of normal aldehydes to branched-chain aldehydes. In one aspect, this invention relates to reacting certain olefinic compounds with carbon monoxide and hydrogen under a specific combination of carefully controlled reaction conditions and in the presence of certain rhodium-containing compositions complexed with tertiary organo-containing phosphorus ligands described hereinafter.

Another aspect of this invention relates to a method for making a hydrocarbon soluble rhodium complex wherein the valence of the rhodium is in the zero state.

Yet another aspect of this invention relates to use of the complex in the condensation and subsequent hydrogenation of the initially formed aldehydes to form the corresponding saturated aldehyde dimers.

Probably the best known catalytic carbonylation reaction is the "oxo" reaction for producing aldehydes and alcohols from carbon monoxide, hydrogen and olefins. Historically, cobalt and rhodium metals and/or complexes incorporating these metals have proven to be superior to other transition metals in catalyzing the hydroformylation of olefins. The ability of rhodium-based catalysts, when compared to cobalt based catalysts, to promote the "oxo" reaction at lower operating pressures and temperatures and catalyst concentrations has been recognized for some time. The oxygenated "oxo" products produced in the presence of rhodium based catalysts are primarily aldehydes.

U.S. Pat. No. 2,880,241 by V. L. Hughes, disclosed that rhodium-containing catalysts are effective for oxygenating olefins thereby permitting "a more selective and different kind of carbonylation".

U.S. Pat. No. 3,329,566 by L. H. Slaugh et al discloses that rhodium carbonyl complexes in the presence of excess phosphine catalyze the "oxo" reaction to give oxygenated products predominating in aldehydes and/or alcohols. Slaugh et al preferred to employ a trialkylphosphine-rhodium-carbonyl complex catalyst at a temperature from about 150°C. to about 210°C. The patentee's examples disclose that their rhodium-catalyzed process results in oxygenated products having an isomer distribution of normal aldehydes to branched-chain aldehydes which are comparable to the cobalt-containing catalyst "oxo" processes.

U.S. Pat. No. 3,527,809 by Roy L. Pruett et al discloses that a hydrido carbonyl tris(triphenylphosphine) rhodium complex [RhH(CO)(Pφ$_3$)$_3$] maintained in solution in the presence of carbon monoxide and hydrogen functions as a catalyst for the hydroformylation reaction. It is the position of this patentee that an excess of triorganophosphorus ligand has to be present in order to get the most preferred results in employing this catalyst system.

Evans, Osborn and Wilkinson disclose in an article entitled "Hydroformylation of Alkenes by Use of Rhodium Complex Catalysts" published in the *Journal of the Chemical Society* (1968) pp. 3133–3142, that complexes of rhodium of the type trans-RhX(CO)(PR$_3$)$_2$ (X = halogen, R = aryl) are used as -hydroformylation catalysts for alkenes.

K. L. Oliver and F. B. Booth in an article entitled "Make Aldehydes by New Oxo Process", published by *Hydrocarbon Processing*, Apr., 1970, pp. 112–114, describe an "oxo" process in which a hydridocarbonyl-tris(triphenylphosphine) rhodium (I) RhH(CO)(φ$_3$P)$_3$ catalyst is employed. An excess of triphenylphosphine is required by this system to realize catalyst stability, as well as to improve n/iso ratio of aldehyde products.

The problem with these prior art rhodium (I) systems is that for the most part under the hydroformylation conditions of the "oxo" process, these complexes are transformed into sparingly soluble carbon monoxide containing complexes and the catalytic activity is known to decrease with time. The resulting partially heterogeneous reaction mixture thus makes catalyst recovery and product handling somewhat more difficult than would a completely homogeneous system.

The rhodium (I complexes can be stabilized to some extent, however, by the addition of excess ligand (5–10 fold excess based on rhodium) but this procedure adds greatly to the cost of the process. Another problem associated with rhodium (I) catalysts systems and especially those containing halide ion, is that a several hour induction period is required to transform the complexes into active catalysts.

Briefly, the subject "oxo" process is carried out in the presence of a zerovalent rhodium compound which may be characterized by one of the following formulas:

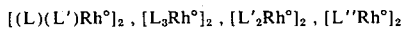

where L is a monodentate ligand, L' is a bidentate ligand and L'' is a tri or quadra-dentate ligand, wherein L, L' and L'' can be the same or different and each is one selected from the group consisting of:

1. R$_3$Q , R$_2$R'Q, (RR'R'')Q

2. R$_2$Q(CR'$_2$)$_x$Q'R$_2$

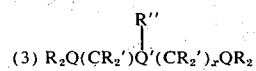

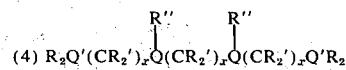

5. RQ'[(CR'$_2$)$_x$QR$_2$]$_2$

6. Q'[(CR'$_2$)$_x$QR$_2$]$_3$ wherein R, R' and R'' can be the same or different and each is selected from the group consisting of hydrogen, F, Cl, Br and I, C$_1$ to C$_{20}$ alkyl, C$_1$ to C$_{20}$ alkoxy, C$_3$ to C$_8$ cycloalkyl, C$_3$ to C$_8$ cycloalkoxy, phenyl, phenyl substituted with F, Cl, Br and I, phenyl substituted with C$_1$ to C$_{20}$ alkyl, phenyl substituted with C$_3$ to C$_8$ cycloalkyl, phenyl substitued substituted C$_1$ to C$_{20}$ alkoxy, oxyphenyl, oxyphenyl substituted with C$_1$ to C$_{20}$ alkyl, oxyphenyl substituted with C$_3$ to C$_8$ cycloalkyl, oxyphenyl substituted with F, Cl, Br and I, oxyphenyl substituted with C$_1$ to C$_8$ cycloalkoxy; Q and Q' can be the same or different and each is selected from the group consisting of P, As and Sb; and x is an integer ranging from 1 to 5.

The catalyst is prepared according to the following equations:

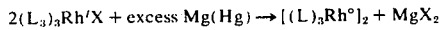

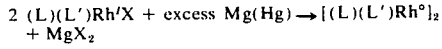

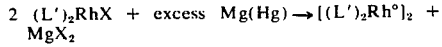

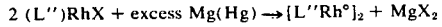

X = Cl, Br, I, F, preferably Cl, Br and I.

The reduction of a rhodium (I) complex is carried out with an excess of magnesium amalgam in the presence of an inert solvent which can be one selected from the group comprising hydrocarbons such as benzene, toluene, n-pentane, ethers such as tetrahydrofuran; diethylether, dioxane, diglyme and triglyme. Magnesium is a unique reducing agent as other more common reducing agents such as sodium and lithium lead to destructive reduction to rhodium metal.

The preferred reaction temperatures range from 0° to 150°C., preferably from 25° to 50°C. and the reaction is carried out in an inert atmosphere wherein a gas such as nitrogen, argon, or neon can be employed. Nitrogen is preferred.

Starting $L_3RLX$, $LL'RhX$, $L'_2RhX$ and $L''RhX$ complexes are well-known in the art and are easily prepared by reacting either olefinic rhodium halogen dimers or rhodium carbonyl halogen dimers with the appropriate Group VA organo ligand in a hydrocarbon solvent such as benzene or hexane. See for example:

1. R. Cramer, *Inorg. Chem.* 1, 722 (1962);
2. M. A. Bennett and G. Wilkinson, *J. Chem. Soc.*, 1418 (1961);
3. S. H. H. Chaston and F. G. A. Stone, *J. Chem. Soc. (A)*, 500 (1969).

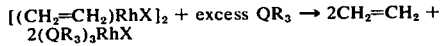

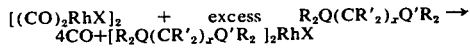

The novel process contemplates employing alpha olefinic compounds as reactants. Such alpha olefinic compounds are characterized by a terminal ethylenic carbon-to-carbon bond which may be a vinylidene group, i.e., $CH_2=C—$; or a vinyl group, i.e., $CH_2=CH—$. They may be straight-chain or branched-chain and may contain groups or substituents which do not essentially interfere with the course of the novel process. Such groups or substituents can be illustrated by carbonyl

carbonyloxy

oxy (—O—), hydroxy (—OH), carboxy (—COOH), halo, alkoxy, phenyl, haloalkyl. The alpha olefinic compound can contain one ethylenic bond or it can contain more than one ethylenic bond. The olefinic linkages may or may not be in conjugation.

Illustrative alpha olefinic compounds which can be employed as reactants include ethylene, propylene, 1-butene, 1-pentene, 1-hexene, 1-heptene, 1-octene, 1-decene, 1-dodecene, 1-octadecene, 2-ethyl-1-hexene, styrene, 3-1-propene, allyl chloride, 1,4-hexadiene, 1,7-octadiene, cyclohexene, 3-cyclohexyl-1-butene, allyl alcohol, hex-1-en-4ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butenoic acid, 7-ocetenoic acid, 3-butenenitrile, 5-hexenamide, and the like. Preferred alpha olefinic compounds include alkenes, alkyl alkenoates, alkenyl alkanoates, alkenyl alkyl ethers, and alkenols, especially those which contain up to 20 carbon atoms. Especially preferred are $C_2$—$C_{10}$ terminal alkenes.

The catalyst is present in the amount ranging from $10^{-6}$ to $10^{-1}$, preferably from $10^{-4}$ to $10^{-2}$ moles, based on the moles of rhodium, per mole of alpha olefinic feed.

It is to be noted that it is preferable to use a small amount of catalyst as possible so as to control the economics in view of the high cost of rhodium metal and rhodium compounds.

The catalyst can be introduced into the process dissolved in a solvent, said solvents are the same as described hereinabove with reference to the preparation of the catalyst.

The required pressures for the hydrogen and carbon monoxide are very low in order to affect a commercial process. The total pressures range from 50 psi to 1000 psi and preferably from 50 psi to 800 psi. A 50/50 volume percent of $CO/H_2$ is preferred but volume percent ranging from 10/90 to 90/10 $CO/H_2$ can be employed. As the relative amount of $H_2$ is increased the carbonylation rate is decreased but hydrogenation of the aldol dimer products is increased. The process can be carried out at temperatures ranging from 50° to 200°C., preferably from 80° to 175°C.

The residence period of the subject process is very critical for if the aldehyde product of the "oxo" reaction is permitted to remain in the autoclave with the reactants for a period of time, say at least 15 minutes, a measurable aldol condensation product results according to the following schematic equation.

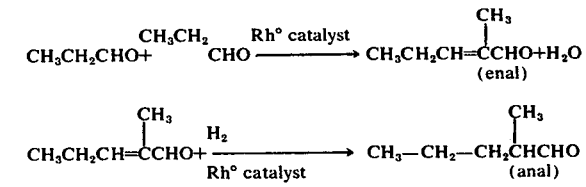

assuming that ethylene was the olefin feed. It is to be noted that this aldol condensation sequence will predominate if the reaction temperature is increased from that under which the initial hydroformylation reaction was carried out. The temperature can be increased ranging from 100° to 200°C., preferably from 150° to 175°C.

The following examples are illustrative. In said examples the procedure generally employed was as follows:

To a pressure vessel there was charged the alpha olefinic compound, if liquid, solvent and rhodium-containing complex. After flushing with argon, the pressure vessel was sealed and then pressurized with carbon monoxide and hydrogen. If a gaseous olefin such as propylene is employed, it is pressured into the autoclave along with hydrogen and carbon monoxide. The reaction temperature was then slowly increased to the desired level. When reaction commenced, a noticeable pressure drop occurred. The pressure was maintained at a predetermined level by the periodic addition of hydrogen and carbon monoxide to the vessel. When the pressure remained essentially constant, the reaction was considered to be complete. Thereafter the vessel and contents were cooled to room temperature, i.e. about 23°C. The excess gases were vented and the vessel was flushed 3 times with argon. The crude reaction mixture was analyzed by a combination of nmr spectroscopy and glc measurements. Samples were also periodically analyzed as the reaction proceeded.

EXAMPLE 1 — Preparation of Zerovalent Rhodium Catalyst

The reduction is carried out in an inert solvent such as benzene or tetrahydrofuran at R.T. An excess of 1% Mg(Hg) (2–10 fold) is employed to insure a rapid rate of reduction. The reaction is conveniently followed by noting the solution of the generally insoluble $L_3RhX$, $(L)(L')RhX$, $L'_2RhX$, $L''RhX$ starting material. The reduction products are isolated by standard techniques and are generally yellow or yellow green solids. The Rh° complexes are air sensitive and must be handled in an inert atmosphere (Ar, $N_2$, Ne). These new Rh° complexes have been well characterized by IR and nmr measurements and elemental analysis.

The procedures hereinbelow were carried out under an $N_2$ atmosphere.

As a typical example 10.0 gms of $((C_6H_5)_3P)_2RhCl$ was placed in 150 ml of dry THF. The resulting dark red slurry was added to a 500 ml r.b. flask containing a Mg(Hg) composed of 1.0 gm Mg dissolved in 100 gm Hg. The reduction was carried out for 24 hours. THF was removed with reduced pressure yielding a yellow brown residue. The residue was extracted with dry benzene yielding a yellow brown solution. A white residue of $MgCl_2$ remained insoluble in benzene. The yellow brown extract was reduced to dryness yielding a yellow-brown residue. Recrystallization of the residue from a 50/50 n-pentane-benzene mixture resulted in the production of a yellow solid consistent with the formula $[((C_6H_5)_3P)_3Rh°]_2$. The yield of the desired Rh° complex are generally in the range of 80–95%. For $[(C_6H_5)P_3Rh°]_2$: % Calc: C, 73.01; H, 5.10; O, nil; Cl, nil; Rh, 11.57; P, 10.47; % Found: C, 72.75; H, 5.13; O, nil; Cl, nil; Rh, 11.52; P, 10.37.

The dimeric nature of the rhodium (O) complex was proven by chemically cleaving $[((C_6H_5)_3P)_3Rh°]_2$ with the stoichiometric amount of $I_2$ yielding two $[(C_6H_5)_3P]_3RhI$ molecules. Also, the $[((C_6H_5)_3P)_3Rh°]_2$ complex is diamagnetic and can only result by forming a dimer via a rhodium-rhodium metal-metal bond.

EXAMPLE 2 — Hydroformylations

All sample preparations were carried out in a dry box employing a nitrogen atmosphere. All solvents were carefully dried and degassed by standard techniques. The hydroformylations were carried out in a Autoclave Engineer's, 300 ml, Magnedrive-Packless, stainless steel autoclave. A valving system was devised that allowed sampling under operating conditions. Reaction mixtures were pressured into the autoclave with argon. A total pressure of 1000 psi (partial pressures of CO and $H_2$ ca. 400 psi) was generally maintained by repressuring the autoclave as the hydroformylation reaction proceeded at a present reaction temperature.

Reaction products were analyzed by glc using a Perkin-Elmer 226 Gas Chromatograph employing a 300 ft. × 0.01 inch stainless steel column internally coated with carbowax K-1540 and equipped with a flame ionization detector and nmr measurements using a Varian-A-60 instrument.

The results of various runs are given in the following Table: In each case the catalyst was pressured into the autoclave either as a solution or a slurry in 70 ml of benzene. Propylene was then added and the mixture brought to reaction temperature. CO and $H_2$ were then added to the desired reaction pressure at a preset reaction temperature. Pseudo first order reaction rates were calculated from the gas consumption versus time data.

TABLE I

| Catalyst | Hydroformylation of Propylene[a] Catalyst (conc)mmole | Cocatalyst | Cocatalyst (conc)mmole | T°C | $C_4H_8O$ (conc)mmole | n/iso | $K \times 10^3$ sec | t 1/2 (min) |
|---|---|---|---|---|---|---|---|---|
| $[((C_6H_5)_3P)_3Rh°]_2$ | 1.1 | — | — | 85 | 0.40 | 65/35 | 1.26 | 9.2 |
| $[((C_6H_5)_3P)_3Rh°]_2$ | 1.1 | $(C_6H_5)_3P$ | 2.0 | 85 | 0.66 | 65/35 | 0.646 | 17.8 |
| $[((C_6H_5)_3P)_3Rh°]_2$ | 1.0 | — | — | 131 | 0.75 | 65/35 | 2.41 | 4.79 |
| $[((C_6H_5)_3P)_3Rh°]_2$ | 1.0 | $(C_6H_5O)_3P$ | 4.0 | 123 | 0.48 | 68/32 | 6.02 | 1.92 |
| $[((C_6H_5O)_3P)_3Rh°]_2$ | 1.0 | — | — | 117 | 0.46 | 62/38 | 0.908 | 12.7 |
| $[((C_4H_9)_3P)_3Rh°]_2$ | 3.0 | — | — | 92 | 0.66 | 65/35 | 0.428 | 7.64 |
| $((C_6H_5)_3P)_3Rh'Cl$[b] | 2.2 | — | — | 132 | 0.59 | 63/37 | 0.636 | 18.2 |
| $((C_6H_5)_3P)_3Rh'Cl$[b] | 2.2 | — | — | 114 | 0.63 | 65/35 | 0.244 | 47.3 |
| $HRh'(CO)(P(C_6H_5)_3)_3$[b] | 1.0 | $(C_6H_5O)_3P$ | 4.0 | 145 | 0.79 | 58/42 | 2.65 | 4.36 |
| $HRh'(CO)(P(C_6H_5)_3)_3$[b] | 1.0 | — | — | 144 | 0.42 | 53/47 | 8.34 | 1.38 |
| $trans[(C_6H_5)_3P]_2Rh'(CO)Cl$[b] | 1.0 | — | — | 137 | 0.31 | 56/44 | 1.70 | 6.79 |
| $[(C_6H_5)_3P]_3Rh'(C_6H_5)$ | 1.1 | — | — | 92 | 0.37 | 65/35 | 0.713 | 16.2 |
| $[(C_6H_5)_2PCH_2CH_2P(C_6H_5)_2]_2Rh'Cl$[b] | 1.0 | — | — | 122 | 0.46 | 46/54 | 0.198 | 58.3 |
| $[(C_6H_5)_2PCH_2CH_2P(C_6H_5)_2]_2Rh°]_2$ | 1.0 | — | — | 122 | 0.41 | | 3.31 | 3.49 |

[a]Total reaction pressure 1000 psi maintained by addition of 50/50 $CO/H_2$.
[b]Heterogeneous reaction mixture.

Table I clearly indicates that rhodium zero phosphine complexes exhibit reaction rates essentially equivalent to and up to 25 times faster than those exhibited by conventional $Rh^I$ complexes. When compared with the commercial "oxo" catalyst $[(C_6H_5)_3P]_3Rh(COh$, however, the rhodium zero complexes of this invention demonstrate a much better n/iso ratio for the product butyraldehydes. These rhodium zero complexes exhibit good hydrocarbon solubility and the "oxo" reaction mixture remains homogeneous throughout the course of the reaction, even at high aldehyde concentrations. The homogeneity of the rhodium zero systems is in marked contrast to the Rh' catalyst systems. The rhodium zero complexes can be recovered unchanged by a simple vacuum distillation and reused without any activity loss. The catalytic activity of the Rh' systems under comparable reaction conditions with the Rh° systems all decrease in activity with time because of irreversible degradation to inactive reaction products. No excess ligand is required by these Rh° catalysts thus a large savings in catalyst cost is achieved. These Rh° catalysts selectively produce butyraldehydes at the conditions given, no alcohols or saturated alkane 3 were detected in the reaction mixture.

EXAMPLE 3 — Condensation of Propanal

In addition to being good hydroformylation catalysts, the Rh° complexes of this invention have been found to promote the aldol condensation and subsequent hydrogenation of the initially formed aldehydes to their corresponding saturated aldehyde dimers. The effective use of Rh° complexes as condensation catalysts is illustrated in the following Table.

By combining steps Ke and $K_H$ with the initial hydroformylation of Cn olefin in a single reaction vessel, a Cn olefin in the presence of $CO/H_2$ and the Rh° complexes can be selectively transformed into a $C(2_{n+2})$ saturated aldehyde.

The percent product balance is based upon the summation of the concentration of unreacted propanal and the desired enal and anal products. The anal product is a desired precursor to plasticizer alcohols.

From the above product distribution as a function of time, the rate of condensation of propanal (expressed as t 1/2 and the subsequent hydrogenation of the enal dimer were found to fall in the ranges Ke = 0.5 to 2.5 hours and $K_H$ = 0.5 to 1.2 hours. Comparable rates were shown by higher normal aldehydes. It was also found that normal aldehydes are condensed at a much faster rate than their branched isomers. For example, in the hydroformylation of propylene where n and iso-butyraldehydes are intermediates, if short reaction times are employed to reduce to the formation of mixed dimers and isodimers, then the condensation product is almost exclusively 2-ethylhexanal. Thus, the uncondensed isobutyraldehyde could be cracked to $H_2O$ and propylene and the propylene recycled.

TABLE II

Condensation of Propanal
Feed: 1.0 mole propanal, 28 ml benzene
Conditions: 175°C.; pCO=300 psi, $pH_2$=520 psi

| Catalyst | Catalyst conc. (mmole) | t hr | Propanal mole | Enal[b] mole | Anal[c] mole | % Product[d] Balance |
|---|---|---|---|---|---|---|
| $[((C_6H_5)_3P)_3Rh°]_2$ | 1.1 | 2.5 | 0.44 | 0.18 | 0.07 | 94 |
|  |  | 4.5 | 0.32 | 0.15 | 0.18 | 98 |
|  |  | 8.5 | 0.24 | — | 0.35 | 94 |
| $((C_6H_5)_3P)_3Rh'Cl$ | 2.2 | 0.5 | 0.98 | — | — | 98 |
|  |  | 2.0 | 0.67 | — | 0.055 | 78 |
|  |  | 6.0 | 0.32 | — | 0.125 | 57[a] |
| $((C_6H_5)_3P)_3Rh'''Cl_3$ | 0.5 | 5.0 | 0.61 | 0.035 | 0.055 | 79[a] |
| $HRh'(CO)[P(C_6H_5)_3]_3$ | 1.1 | 1.5 | 0.43 | 0.14 | 0.045 | 80[a] |
|  |  | 4.5 | 0.22 | — | 0.31 | 84 |
| $HRh'(CO)[P(C_6H_5)_3]_3+$ $(C_6H_5)_3P$ }[e] | {1.0 2.0 | 1.0 2.0 | 0.50 0.31 | 0.16 0.29 | 0.01 0.015 | 90 92 |
|  |  | 5.0 | 0.15 | 0.35 | 0.045 | 94 |
| $Co_2(CO)_8$ | 1.1 | 2.5 | 0.74 | 0.048 | 0.014 | 86[a] |
|  |  | 4.5 | 0.64 | 0.085 | 0.014 | 84 |
|  |  | 8.5 | 0.50 | 0.10 | 0.024 | 75 |
| $[[(C_6H_5)_2PCH_2CH_2P(C_6H_5)_2]_2Rh°]_2$[f] | 1.0 | 0.25 | 0.43 | 0.125 | 0.140 | 96 |
|  |  | 1.25 | 0.25 | — | 0.325 | 90 |
|  |  | 1.75 | 0.22 | — | 0.340 | 90 |
| Feed: 1.0 mole propanal, 70 ml benzene Conditions: 175°C., pCO 350 psi; $pH_2$ 850 psi | | | | | | |
| $[((C_6H_5)_3P)_3Rh°]_2$ | 0.55 | 18 | 0.13 | trace | 0.42 | 97 |
| $(C_6H_5)_3P$ | 1.8 | 18 | 0.99+ | trace | — | 99+ |
| Feed: 1.0 mole propanal, 70 ml benzene Conditions: 125°C., pCO=350 psi; $pH_2$=850 psi | | | | | | |
| $[((C_6H_5)_3P)_3Rh°]_2$ | 0.55 | 17 | 0.28 | trace | 0.35 | 98 |
| $((C_6H_5)_3P)_3Rh'Cl$ | 1.3 | 18 | 0.99+ | trace | trace | 99+ |
| $Rh'''Cl_3 \cdot 3H_2O$ | 1.2 | 19 | 0.80 | trace | trace | 80[a] |

[a]The relatively poor product balance is due to the hydrogenation of the aldehyde to propanol and/or the production of higher molecular weight condensates.
[b]enal = 2-methyl pent-2-enal
[c]anal = 2-methyl pentanal
[d]% product balance based upon unreacted $C_3H_6O$ and the enal and anal products.
[e]Commercial catalyst composition — poor yield of desired anal
[f]Condensation carried out at 150°C.

The desired reaction is described by the following equations:

Trimers and higher condensates become appreciable only after extended reaction times at elevated temperatures. This represents the first disclosure whereby an

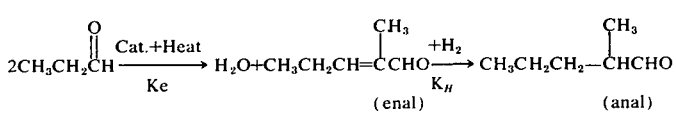

aldehyde is selectively condensed to its corresponding dimer and then hydrogenated solely by the action of a soluble rhodium zero complex. Hydroaldolization is a well known reaction but a strong base such as KOH has always before been needed in conjunction with a transition metal hydrogenation catalyst to effect the desired condensation - hydrogenation reaction sequence. Although one $Rh^I$ complex, namely, $HRh(CO)(P(C_6H_5)_3)_3$, was found to condense propanal the product balance demonstrated by this catalyst is relatively poor. More importantly, the commercial hydroformylation of olefins with $HRh(CO)(P(C_6H_5)_3)_3$ is carried out in the presence of excess phosphine so as to stabilize the $Rh^I$ catalyst. This system forms only very small amounts of the desired anal product and thus it would be economically unwise to use this catalyst mixture for the production of anol. Other $Rh^I$ and $Rh^{III}$ complexes treated do not selectively dimerize aldehydes but instead produce alcohols (propanol) and/or mixtures of higher condensates.

In effect then, by combining the initial hydroformylation step with steps $K_e$ and $K_H$ described above in a single reaction vessel, a Cn terminal olefin in the presence of $CO/H_2$ and the $Rh^\circ$ complexes can be selectively transformed in $C(2_{n+2})$ saturated aldehydes. This represents a very substantial improvement over present day technology which uses a multistep process which is characterized by (1) initial hydroformylation using Co or Rh catalysts, (2) fractional distillation of hydroformylation products to separate n and iso aldehydes, (3) base (KOH) condensation of the n-isomer to form the enal, (4) fractional distillation of enal product, and (5) hydrogenation of enal to anol over a precious metal catalyst such as Ni or Pt.

What is claimed is:

1. A process for the production of normal aldehydes which comprises the step of contacting an alpha olefinic hydrocarbon having up to 20 carbon atoms at a temperature ranging from 50° to 175°C. and a pressure ranging from 10 to 1000 psi with carbon monoxide and hydrogen in the presence of a catalyst wherein the amount of catalyst ranges from $10^{-6}$ to $10^{-1}$ mols of rhodium per mol of alpha olefinic hydrocarbon and wherein said catalyst composition is characterized as one of the following zero-valent rhodium complexes:

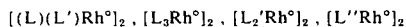

where L is a monodentate phosphine ligand, L' is a bidentate phosphine ligand and L" is a tri or quadradentate phosphine ligand, wherein L, L' and L" is the same or different and each is one selected from the group consisting of:

1. $R_3P$, $R_2R'P$, $(RR'R'')P$

2. $R_2P(CR_2')_xP R_2'$

3. $R_2P(CR_2')_x\overset{R''}{P}(CR_2')_xPR_2'$

4. $R_2P(CR_2')_x\overset{R''}{P}(CR_2')_x\overset{R''}{P}(CR_2')_xPR_2'$

5. $R''P[(CR_2')_xPR_2'']_2$

6. $P[(CR_2')_xPR_2]_3$ wherein R, R' and R'' can be the same or different and each is selected from the group consisting of hydrogen, F, Cl, Br and I, $C_1$ to $C_4$ alkyl, to $C_4$ alkoxy, $C_3$ to $C_8$ cycloalkyl, $C_3$ to $C_8$ cycloalkyl, phenyl, phenyl substituted with F, Cl, Br and I, phenyl substituted with $C_1$ to $C_4$ alkyl, phenyl substituted with $C_3$ to $C_8$ cycloalkyl, phenyl substituted with $C_1$ to $C_4$ alkoxy, oxyphenyl, oxyphenyl substituted with $C_1$ to 132 20$C_4$ alkyl, oxyphenyl substituted with $C_3$ to $C_8$ cycloalkyl, oxyphenyl substituted with F, Cl, Br and I, oxyphenyl substituted with $C_1$ to $C_8$ cycloalkoxy; can be the same or different and each is selected from the and $x$ is an integer ranging from 1 to 5.

2. A process according to claim 1 wherein the 2 alpha olefin is a $C_{2C10}$ alkene.

3. A process for the production of normal aldehydes which comprises the step of contacting propylene with carbon monoxide at a temperature ranging from 50° to 175°C and a pressure ranging from 10 to 1000 psi in the presence of a catalyst characterized as $[((C_6H_5)_3P)_3Rh^\circ]_2$.

4. A process according to claim 3 wherein the catalyst is characterized as $[(C_4H_9)_3P)_3Rh^\circ]_2$.

5. A process according to claim 3 wherein the catalyst is characterized as $[((C_6H_5O)_3P)_3Rh^\circ]_2$.

6. A process according to claim 3 wherein the catalyst is characterized as $[[(C_6H_5)_2PCH_2CH_2P(C_6H_5)_2]_2Rh^\circ]_2$.

* * * * *